United States Patent
Lin et al.

(10) Patent No.: US 9,511,341 B2
(45) Date of Patent: Dec. 6, 2016

(54) METHOD FOR PREPARING ACETAZOLAMIDE SODIUM POWDER

(71) Applicant: SCI Pharmtech, Inc., Taoyuan (TW)

(72) Inventors: Yen-Chih Lin, Taoyuan (TW); Yon-Lian Wu, Taoyuan (TW)

(73) Assignee: Sunny Pharmtech Inc., New Taipei (TW)

( * ) Notice: Subject to any disclaimer, the term of this patent is extended or adjusted under 35 U.S.C. 154(b) by 559 days.

(21) Appl. No.: 14/014,823

(22) Filed: Aug. 30, 2013

(65) Prior Publication Data

US 2015/0061169 A1 Mar. 5, 2015

(51) Int. Cl.
*B01J 13/04* (2006.01)
*A61K 9/00* (2006.01)

(52) U.S. Cl.
CPC ............... *B01J 13/043* (2013.01); *B01J 13/04* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 6,113,941 A * | 9/2000 | Takada | A61K 9/1647 424/426 |
| 6,763,607 B2 * | 7/2004 | Beyerinck | A61K 9/146 34/372 |
| 8,216,495 B2 | 7/2012 | Janssens et al. | |
| 2006/0024374 A1 | 2/2006 | Gasco et al. | |
| 2007/0020336 A1 | 1/2007 | Loftsson et al. | |
| 2008/0311162 A1 | 12/2008 | Darmuzey et al. | |
| 2009/0098200 A1 | 4/2009 | Temtsin Krayz et al. | |
| 2013/0059795 A1 | 3/2013 | Lo et al. | |

* cited by examiner

*Primary Examiner* — Benjamin Schiffman
(74) *Attorney, Agent, or Firm* — Leydig, Voit & Mayer, Ltd.

(57) ABSTRACT

A method for preparing acetazolamide sodium powder for injection is provided. The method includes steps of providing an acetazolamide sodium solution; and aseptically spray drying the acetazolamide sodium solution to obtain the acetazolamide sodium powder.

11 Claims, 5 Drawing Sheets

METHOD FOR PREPARING ACETAZOLAMIDE SODIUM POWDER

FIELD OF THE INVENTION

This invention relates to a method for preparing powder for injection. In particular, the present invention relates to a method for preparing acetazolamide sodium powder by spray drying.

BACKGROUND OF THE INVENTION

Acetazolamide sodium (ACZ.Na) powder is a parenteral dosage form of acetazolamide, which is a carbonic anhydrase inhibitor and used to lower the intraocular pressure. Thus, the acetazolamide sodium is mainly used for treating glaucoma. Other indications include epilepsy, congestive heart failure, drug-induced edema, and mountain sickness. In some reports, the acetazolamide (ACZ) is present in two crystal structures, such as triclinic and monoclinic. The triclinic structure is commercially available due to the thermodynamic stable at 20° C. Generally, the acetazolamide is granulated into tablet and administered through oral route. Since the acetazolamide has an extremely low solubility in water, the bioavailability of acetazolamide tablet is regarded as an issue. However, the acetazolamide sodium shows a different characteristic on solubility. The acetazolamide sodium powder easily dissolves in water so as to be reconstituted as injectable dosage form. Therefore, the acetazolamide sodium has much higher bioavailability than acetazolamide.

In the commercial acetazolamide sodium powder, i.e., acetazolamide for injection, it is obtained from lyophilizing 10% (w/v) solution of acetazolamide sodium. The lyophilizing process includes freezing a constituted solution (freezing stage), sublimating ice (primary drying stage), and removing solvent (secondary drying stage). In the freezing stage, the temperature of solution is adjusted below the eutectic temperature of solution. After the freezing stage, the pressure of drying chamber is reduced to a value required for sublimating water and meanwhile a significant heat is supplied as the latent heat for sublimating water. In the final stage, the pressure is further reduced and the temperature is slightly increased to remove the bound water, which is about 10-35% of total water contents. In the view of the whole process, lyophilization costs more due to the needs of refrigeration, vacuum, and long cycle times. As a result, lyophilization costs about 5-10 times higher than spray drying, which is generally adopted in chemical industry but rarely used in manufacturing a pharmaceutical powder for injection.

Spray drying is one of the conventional techniques in chemical industry since 1920s and has several advantages in comparison with the lyophilization. For example, the spray drying can save more than 50% energy than the lyophilization. In general, the spray drying primarily includes three stages. Firstly, a concentrated solution is atomized into numerous liquid droplets. Then, the liquid droplets contact the heated gas, e.g., air or nitrogen ($N_2$), and then the liquid droplets evaporate to accompany with the nucleation of particles in a short period (such as about a few seconds). Finally, the dried particles are collected by a cyclone system incorporated with a bag filter or wet scrubber. In view of the industrial process, the advantages for spray drying include the continuous mass production, automated controlling, higher energy efficiency, and feasible applications of both heat-resistant and heat-sensitive materials. Therefore, spray dryers are widely applied in various industries. However, it is rarely applied for manufacturing active pharmaceutical ingredients (APIs) in pharmaceutical industry. In the reported literatures, there are some disclosures related to spray drying of acetazolamide, but that of acetazolamide sodium has not been disclosed yet. The follows are some prior arts related to spray drying acetazolamide.

US2006/0024374 discloses a process for preparing solid lipid nanoparticles (SLNs), which includes 0.1% to 7.0% of a pharmacologically active substance. Acetazolamide was disclosed as one of the pharmacologically active substances. In the disclosed process, the SLNs dispersion is prepared by microemulsion, precipitation, and washing. Then the resultant SLNs dispersion is dried by lyophilization, spray drying, or evaporation to obtain the SLNs with the drug incorporated.

US2007/0020336 discloses an ophthalmic composition, which is an aqueous suspension comprising an active pharmaceutical ingredient (API), cyclodextrin, and water. One of the disclosed APIs is acetazolamide. Moreover, the ophthalmic composition powder can be obtained by lyophilizing or spray drying the disclosed aqueous suspension.

US2008/0311162 discloses a compacting method of making a solid composition comprising at least one film enrobing a compacted fill material having a pressure sensitive multiparticulate and/or a cushioning agent. Among the disclosed pressure sensitive multiparticulates, acetazolamide is one of the candidates and can be prepared by granulation, spray drying, lyophilization, and the like. However, no more details about the spray drying are reported.

US2009/0098200 discloses a solid composition comprising at least one lipophilic active compound and two or more polymers. It is disclosed that acetazolamide is one of diuretics as the lipophilic active compound. Moreover, the composition can be prepared by a method comprising the steps of (i) providing a clear and homogeneous solution of at least one lipophilic active compound and two or more polymers in a mixture of water and an organic solvent; and (ii) spray drying the constituted solution of (i) to form a dry powder.

US2013/0059795 discloses a drying method for preparing a composition comprising a leaf protein-lipid-soluble material complex, in which the lipid-soluble materials includes acetazolamide and other drug substances. According to the disclosed technique, a suspension of leaf protein in water is constructed and then mixed with the solution of lipid-soluble material in organic solvent. After mixing, the mixture is dried by freezing-drying, precipitation, or spray drying to form the leaf protein-lipid-soluble material complex powder.

U.S. Pat. No. 8,216,495 discloses a spray drying method for preparing a solid dispersion comprising polyvinyl alcohol-polyethylene glycol graft copolymer and biopharmaceutical classification system (BCS) class II or IV drug. The copolymer is dissolved in a water/first alcohol mixture. Then, the drug is dissolved in a mixture of a second alcohol and non-alcoholic organic solvent. Subsequently, the constituted solutions are mixed and then spray dried to produce the solid dispersion.

The above spray drying methods are mainly utilized for preparing solid composition comprising acetazolamide and at least one excipient, such as lipid, cyclodextrin, protein, and polymer. In order to prepare the composite material, US2007/0020336 discloses an aqueous suspension system in the spray drying process because of the limitation of extremely low solubility of acetazolamide in water. Although the ophthalmic composition powder can be prepared, the particle size and crystal structure of acetazolamide will be invariable by such a spray drying method. On the other hand, various conventional methods utilize the organic solvent to overcome the demerit of solubility. However, the organic solvent will evolve another drawback, i.e., the residual solvent, which is harmful to human body.

Among the above spray drying methods for preparing acetazolamide, the hydrolysis reaction of acetazolamide does not occur in the process because of the application of organic solvent or insoluble acetazolamide in water. However, hydrolysis is a considerable attribute in the process of manufacturing acetazolamide sodium. As a result, lyophilization is applied to manufacturing the commercial product of acetazolamide for inejction.

Hence, this invention provides a spray drying method for preparing acetazolamide sodium powder as the acetazolamide for injection to replace the commercialized technique, i.e., lyophilization. Accordingly, the present invention provides a method for preparing acetazolamide sodium powder that can be formulated as acetazolamide for injection and reconstituted for intravenous administration by spray drying.

SUMMARY OF THE INVENTION

The present invention provides a method for preparing an acetazolamide sodium powder for injection. The method includes steps of: providing an acetazolamide sodium solution; and aseptically spray drying the acetazolamide sodium solution to obtain an acetazolamide sodium powder that can be collected by a cyclone system incorporated with a wet scrubber. The prepared acetazolamide sodium powder can be formulated as acetazolamide for injection and reconstituted for intravenous administration.

Preferably, the acetazolamide sodium solution of the present invention is prepared by the following steps of: dispersing an acetazolamide powder in water to obtain an acetazolamide suspension; mixing the acetazolamide suspension with a sodium hydroxide solution to obtain an acetazolamide sodium solution; and aseptically filtrating the acetazolamide sodium solution by a filter with a pore size smaller than 0.22 μm.

Preferably, the acetazolamide powder has a crystal structure which is selected from the group consisting of a triclinic form, a monoclinic form and a combination thereof.

Preferably, the sodium hydroxide solution and the acetazolamide suspension are mixed in a molar ratio range from 1.60 to 1.95.

Preferably, the acetazolamide sodium solution has a concentration of acetazolamide sodium in a range from 5 wt % to 40 wt %. In one embodiment of the present invention, the acetazolamide sodium solution is kept at a temperature below 30° C.

Preferably, the spray drying is performed with a drying gas. In one embodiment of the present invention, the drying gas is air or nitrogen ($N_2$). In another embodiment of the present invention, the temperature of the drying gas is in a range from 100° C. to 250° C. .

Preferably, the acetazolamide sodium powder has an amorphous structure or a partially amorphous structure.

In accordance with the embodiments of the present invention, the method is provided for preparing acetazolamide sodium powder that can be formulated as acetazolamide for injection and reconstituted for intravenous administration.

DETAILED DESCRIPTION OF THE PREFERRED EMBODIMENT

The present invention provides a method for preparing the acetazolamide sodium powder by spray drying and such powder can be used as acetazolamide for injection or reconstituted for intravenous administration. The following examples are offered to illustrate, but not to limit the claimed invention.

In various aspects of embodiments of the present application, the contents of related compounds in acetazolamide met the requirement of United States Pharmacopeia (USP). In addition, the sodium hydroxide and water for injection were provided by a local supplier.

In the preferred embodiments, the spray dryer, SD-06AG, made by LabPlant Ltd. mainly comprises an atomizer, a heater, a blower, a drying chamber and a cyclone. The gas-liquid flow type can be co-current or mix-flow. A wet scrubber is also connected to the exit of cyclone in order to recover the uncollected spray dried powder.

In one embodiment, the acetazolamide sodium solution was constituted at a pH in a range from 9.0 to 10.0 in accordance with the molar ratio of sodium hydroxide to acetazolamide.

In the developed spray drying process, the spray dryer was initiated in the preferred conditions (such as temperature and flow rate of the heated gas, and pneumatic pressure). In the meantime, an acetazolamide sodium solution was prepared by dispersing the acetazolamide powder into water in a flask inerted with $N_2$ and then mixing the acetazolamide suspension with sodium hydroxide solution. After stirring for 15 min, an acetazolamide sodium solution was obtained and pumped into the spray dryer to proceed the drying process. During the drying process, the acetazolamide sodium solution was fed and atomized into mist by a two-fluid nozzle, and then the water was rapidly vaporized and accompanied with the nucleation of acetazolamide sodium particles in the gas flow of drying chamber. The formed particles were immediately carried into the cyclone, in which the separation of gas-solid was performed. The uncollected particles were recovered by the wet scrubber connected to the exit of cyclone. Finally, the acetazolamide sodium powder in the collector was examined by a halogen moisture analyzer and an analytical HPLC method specified in the current USP monograph of acetazolamide for injection.

EXAMPLE 1

Figure 1:
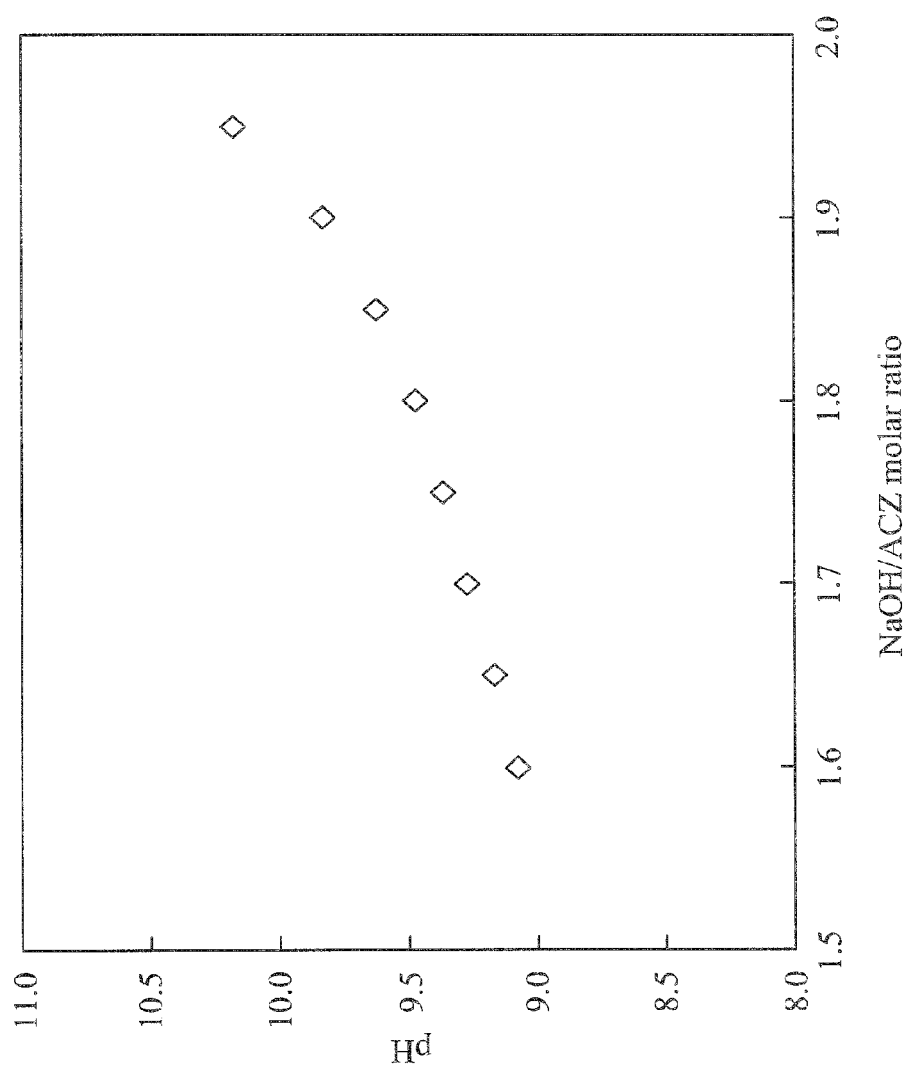
FIG. 1 shows the effect of molar ratio of sodium hydroxide to acetazolamide on the pH of constituted acetazolamide sodium solution.

The molar ratio of sodium hydroxide to acetazolamide (NaOH/ACZ) in the 10% constituted solution was controlled at about 1.60 to about 1.95 as shown in FIG. 1.

In accordance with the specified molar ratio of NaOH/ACZ, the acetazolamide sodium solution had a concentration of about 5 wt % to about 40 wt %, and more particularly about 6 wt % to about 30 wt %. In constituting the acetazolamide sodium solution, the system was inerted with $N_2$ in order to prevent the acetazolamide sodium solution from contacting with air or oxygen and the temperature for constituting the solution was isothermal at below 30° C., more particularly below 20° C.

6.5 wt % and 27.4 wt % of the acetazolamide sodium solutions with a NaOH/ACZ molar ratio of 1.74 at 5° C. were spray dried in the mix-flow or co-current type by using air as the drying gas with the inlet temperature at 240° C., 392 ml/h liquid flow rate, and 42 CMH gas flow rate. The results shown in Table 1 represented that a thick solution having higher viscosity was atomized poorly so that the adhesion of liquid droplets on the wall of drying chamber became significant and a lower yield was obtained. To the extent of the differences in water contents of the spray dried powders, it was directly affected by the quantity of vaporized water. Thus, the powder with a lower water content (about 5.1%) was formed by spray drying a thick solution. In addition, each of acetazolamide sodium powder was reconstituted with water for injection and the pH was between 9.31 and 9.33, which met the pH requirement of acetazolamide for injection in USP.

Figure 2:
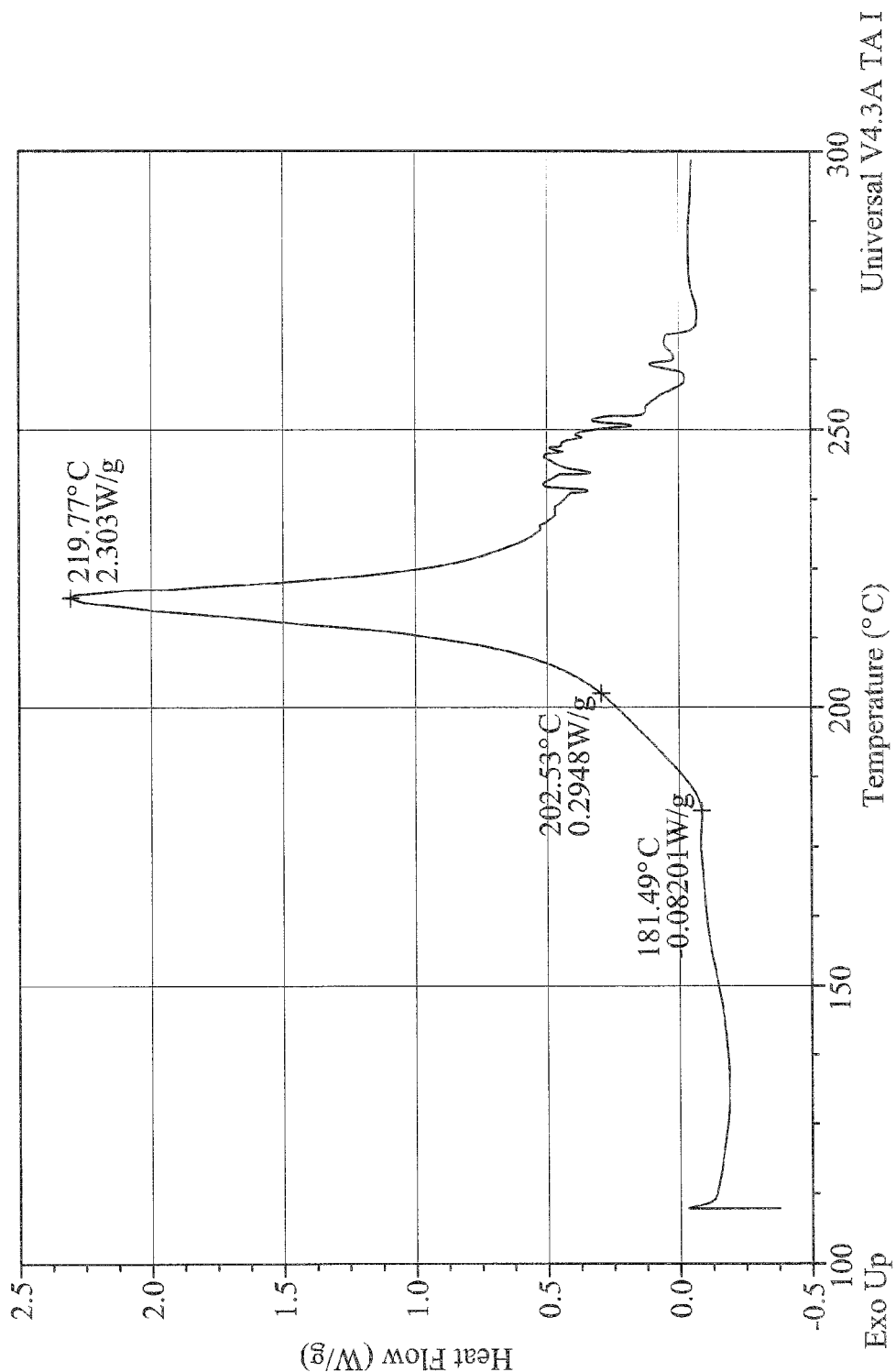
FIG. 2 shows a differential scanning calorimetry thermogram of spray dried acetazolamide sodium powder.
Figure 3:
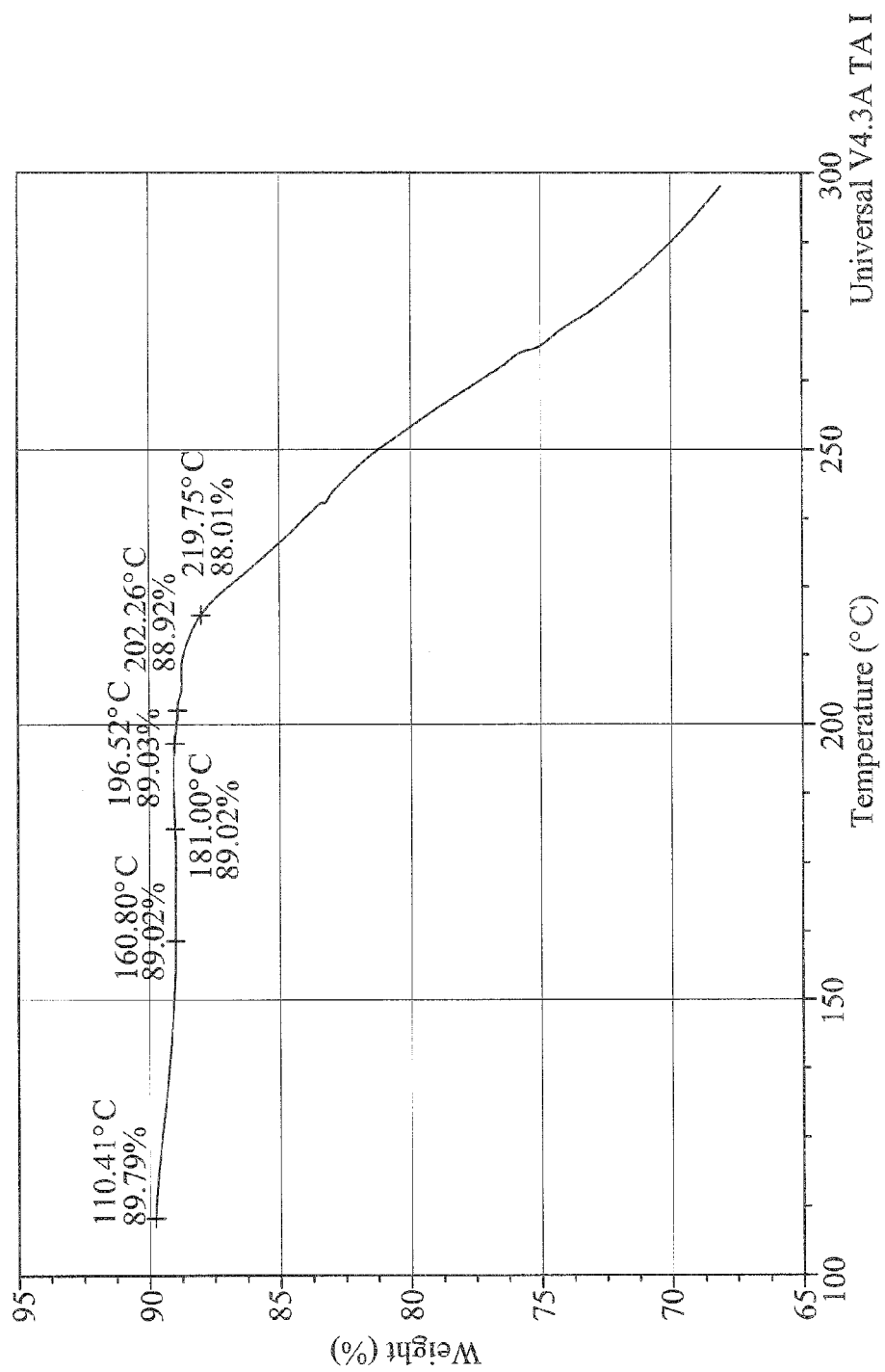
FIG. 3 shows a thermogravimetric analysis for spray-dried acetazolamide sodium powder.

The resulting acetazolamide sodium powder from Test 1-1 was analyzed by DSC and TGA instruments to characterize the thermal properties. The results shown in FIGS. 2 and 3 revealed that the acetazolamide sodium powder decomposed at temperature higher than 180° C. and the exothermic peak of decomposition was at about 220° C.

EXAMPLE 2

In Example 2, the amount of impurity D in the acetazolamide free base was about 0.098-0.110 wt %. The spray drying was performed by using $N_2$ and air as heated gas in comparison with the effect of humidity and oxygen on the acetazolamide sodium powder.

In Table 2, the results showed that the spray dried acetazolamide sodium powder was not oxygen-sensitive due to the negligible difference of impurity D. On the other hand, the moisture in the acetazolamide sodium powder was reduced while using $N_2$ as the drying gas.

TABLE 2

| | ACZ.Na concentration (wt %) | Inlet temp. (° C.) | Outlet temp. (° C.) | Flow type | Drying Gas | Liquid flow Rate (ml/h) | Impurity D* (%) | LOD (%) | Yield (%) (dried basis) | Reconstitution pH (1 g dried powder/10 ml WFI) |
|---|---|---|---|---|---|---|---|---|---|---|
| Test 2-1 | 27.4 | 200 | 109 | Mix-flow | Air | 392 | 0.122 | 5.2 | 66 | 9.30 |
| Test 2-2 | 27.4 | 200 | 110 | Mix-flow | $N_2$ | 392 | 0.124 | 2.5 | 60 | 9.30 |

*Impurity D represents 5-amino-1,3,4-thiadiazole-2-sulfonic acid, which is the product hydrolyzed from acetazolamide sodium.

EXAMPLE 3

In Example 3, the acetazolamide free base with about 0.036 wt % impurity D was applied. Two drying temperatures were chosen to investigate whether the acetazolamide sodium was heat-sensitive during the spray drying process. In Table 3, the results of Test 3-1 and Test 3-2 showed that the amounts of impurity D slightly increased to 0.041% and 0.047%, respectively. Moreover, the acetazolamide sodium powders were reconstituted with water for injection to form the 10% (w/v) solutions with pH 9.36 and 9.38, respectively.

In order to remove the remaining water in the powder, the collected powder in Test 3-2 was further dried by a rotary evaporator in vacuum at 40° C. for 15 hours. As a result, the water reduced from 3.1% to 1.4% and the amount of impurity D only slightly increased from 0.047% to 0.054%.

Figure 4:
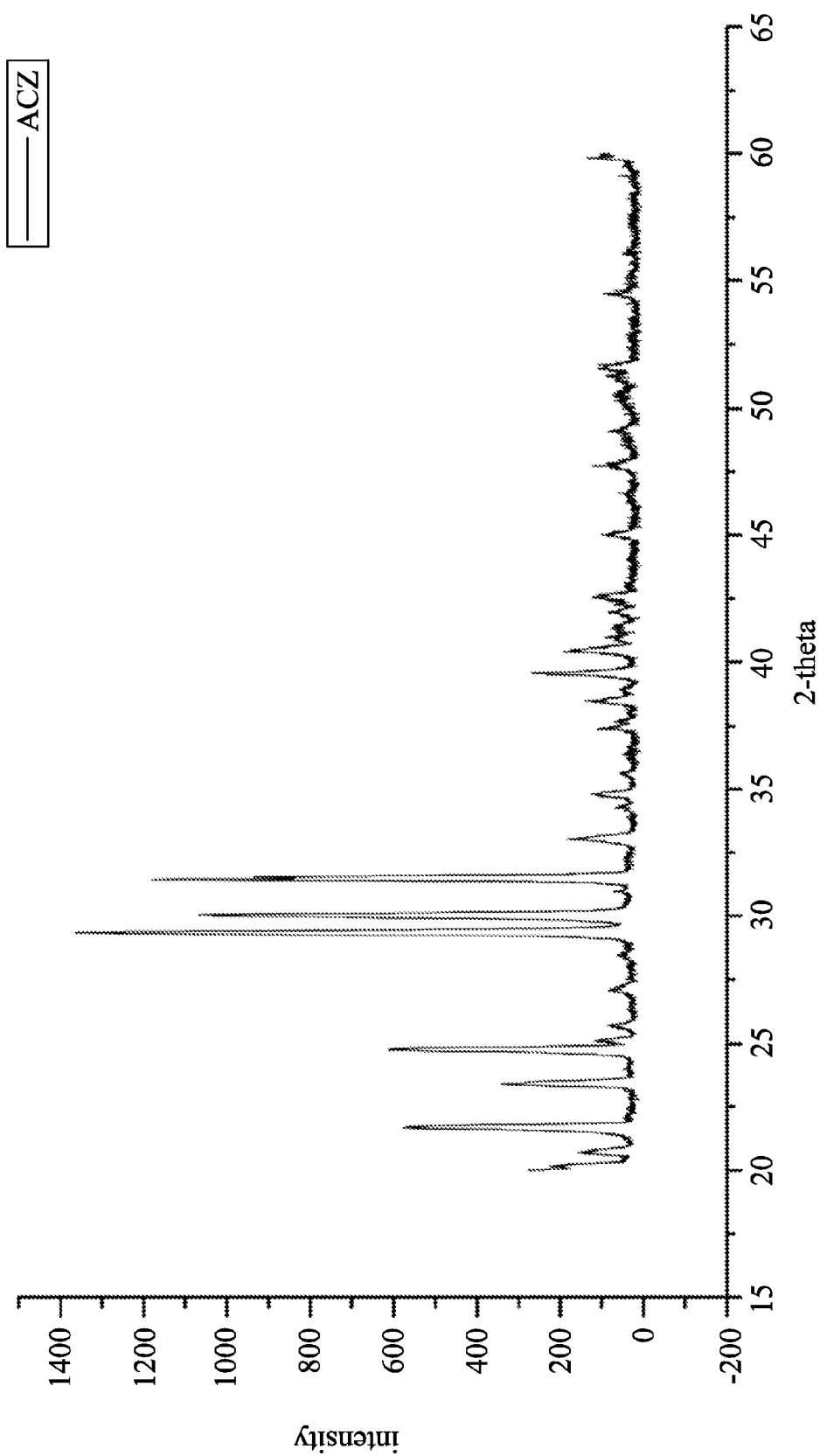
FIG. 4 shows a X-ray diffraction pattern of acetazolamide powder.
Figure 5:
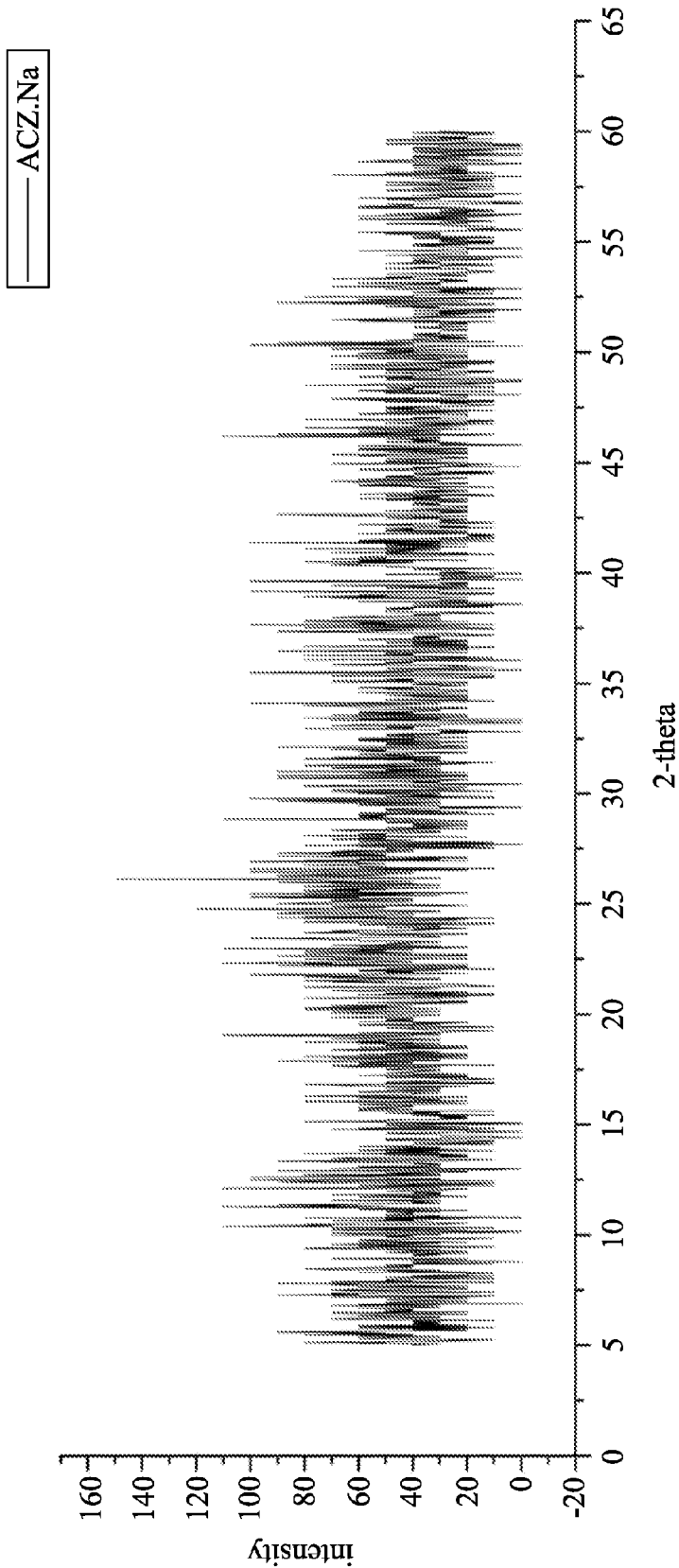
FIG. 5 shows a X-ray diffraction pattern of spray dried acetazolamide sodium powder.

Furthermore, the acetazolamide free base powder and spray dried acetazolamide sodium powder with 1.4% residual water were analyzed by X-ray diffractometer, and the resulting diffraction patterns were shown in FIGS. 4 and 5, respectively. Apparently, the spray dried acetazolamide sodium powder was mainly in an amorphous form.

TABLE 1

| | ACZ.Na concentration (wt %) | Inlet temp. (° C.) | Outlet temp. (° C.) | Flow type | Drying Gas | Liquid flow Rate (ml/h) | LOD* (%) | Yield (%) (dried basis) | Reconstitution pH (1 g dried powder/10 ml WFI) |
|---|---|---|---|---|---|---|---|---|---|
| Test 1-1 | 27.4 | 240 | 115 | Mix-flow | Air | 392 | 5.1 | 63 | 9.31 |
| Test 1-2 | 6.5 | 240 | 109 | Mix-flow | Air | 392 | 7.8 | 74 | 9.33 |
| Test 1-3 | 27.4 | 240 | 113 | Co-current | Air | 392 | 5.5 | 65 | 9.33 |

*LOD: Loss on drying

TABLE 3

| | ACZ.Na concentration (wt %) | Inlet temp. (° C.) | Outlet temp. (° C.) | Flow type | Gas | Liquid flow Rate (ml/h) | Impurity D* (%) | LOD (%) | Yield (%) (dried basis) | Reconstitution pH (1 g dried powder/10 ml WFI) |
|---|---|---|---|---|---|---|---|---|---|---|
| Test 3-1 | 27.4 | 200 | 98 | Mix-flow | $N_2$ | 392 | 0.041 | 4.9 | 44 | 9.36 |
| Test 3-2 | 27.4 | 240 | 115 | Mix-flow | $N_2$ | 392 | 0.047 | 3.1 | 49 | 9.38 |

*Impurity D represents 5-amino-1,3,4-thiadiazole-2-sulfonic acid, which is the product of hydrolysis of acetazolamide sodium.

It is to be understood that the invention is not limited to the preferred embodiments, though the invention has been described in terms of the various embodiments. Moreover, it is intended to cover various modifications and similar structures contained within the spirit and scope of the appended claims, which are to be accorded with the broadest interpretation so as to encompass all such modifications and similar variations.

What is claimed is:

1. A method for preparing an acetazolamide sodium powder for injection, comprising steps of:
   providing an acetazolamide sodium solution prepared by dispersing an acetazolamide powder in water to obtain an acetazolamide suspension and mixing the acetazolamide suspension with a sodium hydroxide solution to obtain an acetazolamide sodium solution; and
   aseptically spray drying the acetazolamide sodium solution through a nozzle, thereby obtaining the acetazolamide sodium powder.

2. The method according to claim 1, wherein the acetazolamide sodium solution is further prepared by
   aseptically filtrating the acetazolamide sodium solution by a filter with a pore size equal to or smaller than 0.22 µm.

3. The method according to claim 2, wherein the acetazolamide powder has a crystal structure which is selected from the group consisting of a triclinic form, a monoclinic form and a combination thereof.

4. The method according to claim 2, wherein a molar ratio of the sodium hydroxide solution to the acetazolamide suspension ranges from 1.60 to 1.95.

5. The method according to claim 2, wherein the acetazolamide sodium solution has 5 wt % to 40 wt % of acetazolamide sodium.

6. The method according to claim 2, wherein the acetazolamide sodium solution is kept at a temperature below 30° C.

7. The method according to claim 6, wherein the acetazolamide sodium solution is kept at a temperature below 20° C.

8. The method according to claim 1, wherein the spray drying is performed with a drying gas.

9. The method according to claim 8, wherein the drying gas is air or nitrogen.

10. The method according to claim 9, wherein a temperature of the drying gas is in a range from 100° C. to 250° C.

11. The method according to claim 1, wherein the acetazolamide sodium powder has an amorphous structure or a partially amorphous structure.

* * * * *